United States Patent [19]

Pollack

[11] 4,140,119

[45] Feb. 20, 1979

[54] BALLOON-TIPPED EXTRACORPOREAL CANNULA APPARATUS AND METHOD FOR INSERTION OF SAME

[76] Inventor: Charles N. Pollack, 12311 Windsor Dr., Carmel, Ind. 46032

[21] Appl. No.: 796,362

[22] Filed: May 12, 1977

[51] Int. Cl.$^2$ .................... A61M 1/03; A61M 25/00
[52] U.S. Cl. ................................ 128/214 R; 128/348; 128/349 B
[58] Field of Search .............................. 128/348–351, 128/246, 240, 219, 214 R, 214.4

[56] References Cited

U.S. PATENT DOCUMENTS

| | | | |
|---|---|---|---|
| 2,919,697 | 1/1960 | Kim | 128/349 B |
| 3,185,151 | 5/1965 | Czorny | 128/214.4 |
| 3,331,371 | 7/1967 | Rocchi et al. | 128/349 B |
| 3,392,722 | 7/1968 | Jorgensen | 128/350 R X |

FOREIGN PATENT DOCUMENTS

| | | | |
|---|---|---|---|
| 465204 | 12/1975 | U.S.S.R. | 128/349 B |

*Primary Examiner*—Dalton L. Truluck
*Attorney, Agent, or Firm*—Woodard, Weikart, Emhardt & Naughton

[57] ABSTRACT

A balloon-tipped extracorporeal cannula apparatus suitable for use in a cardiac cannulation technique including a first elongated and flexible tube having an open proximal end and a closed distal tip with a plurality of holes near the distal end, an inflatable balloon on the inside wall of the first tube adjacent to and proximal of the holes, and a second flexible tube contacting the balloon for readily inflating and deflating the balloon. When inflated, the balloon completely occludes the lumen of the first tube and extends to a point between the most distal portion and the most proximal portion of the holes near the distal end of the first tube thereby only partially obstructing the holes. In addition, a method for inserting a balloon-tipped extracorporeal cannula during a cardiac cannulation technique comprising filling the lumen of the cannula with fluid, inflating the balloon on the inside wall of the cannula near the holes at its closed distal tip, inserting the distal end of the cannula into the circulatory system of the person through a prepared incision and deflating the balloon thereby allowing fluid to flow between the cannula and the circulatory system.

12 Claims, 6 Drawing Figures

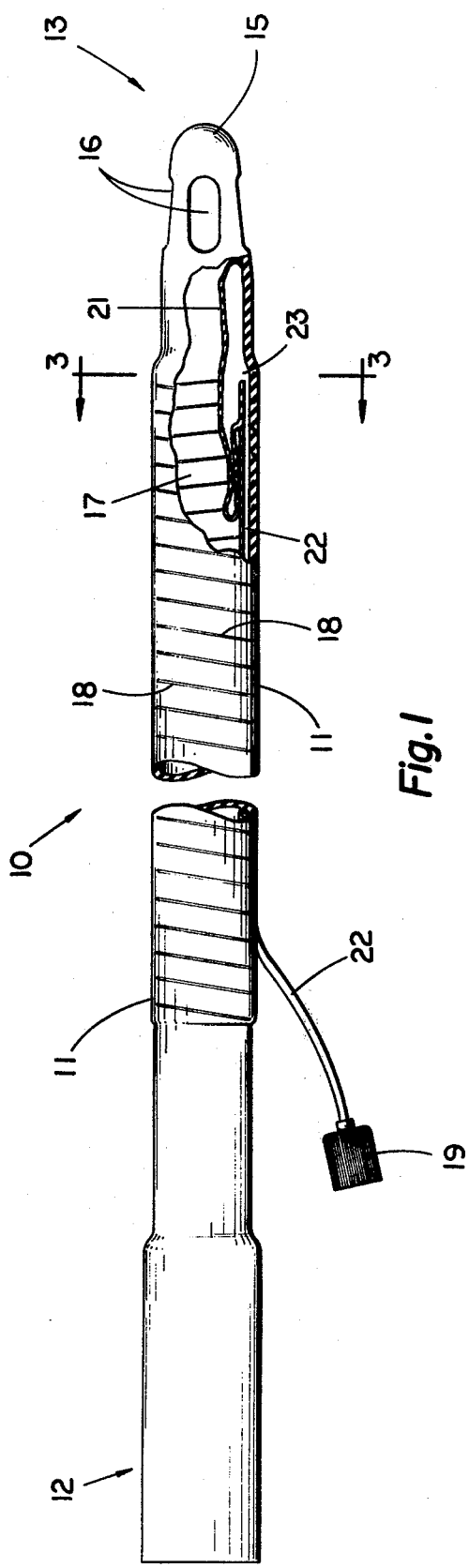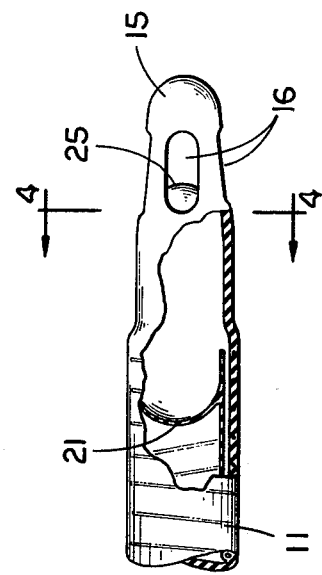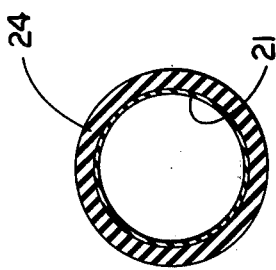

BALLOON-TIPPED EXTRACORPOREAL CANNULA APPARATUS AND METHOD FOR INSERTION OF SAME

BACKGROUND OF THE INVENTION

1. Field of the Invention

This invention relates to methods and apparata used in cannulation techniques, and particularly, to an improved cannula apparatus and method for its insertion suitable for use in a cardiac cannulation technique.

2. Description of the Prior Art

A cannula, or catheter as it may be called, is generally recognized as an elongated and flexible tube that may be inserted into a person's body in order to withdraw or inject various fluids. The prior art is replete with such cannulas and catheters, as well as with methods for their insertion and use.

The use of inflatable balloons with such cannulas and catheters is also known in the art. In one instance, commonly referred to as a "bag" catheter, an externally-attached balloon or "bag" is used to hold the catheter in place after insertion in order to allow prolonged or periodic withdrawal or injection of fluids into the body. A common use for such "bag" catheters, as disclosed in Rocchi et al., U.S. Pat. No. 3,331,371, is to insert the catheter by way of the urethra into a person's bladder in order to withdraw fluid from the bladder over a protracted period of time. Another example of an externally-attached inflatable balloon or collar used to stabilize the position of the cannula following insertion is found in Shinnick et al., U.S. Pat. No. 3,680,544, which discloses a transthoracic cannula-type device useful in cardiopulmonary resuscitation.

In other instances, inflatable balloons have been positioned inside the luminal cavity in the cannula or catheter in order to achieve a desired result. In Kim, U.S. Pat. No. 2,919,697, such an intraluminal inflatable balloon was used for the same purpose as above described, i.e., for anchoring the standard catheter drainage tube in the body after insertion. The above Rocchi reference, on the other hand, uses the intraluminal balloon or ball to completely cover the fluid entrance holes in the catheter and thereby control the flow of fluid therethrough.

A rapidly-growing area of cannula technology concerns the technique of cardiac cannulation and the use of artificial heart-lung machines to facilitate intricate and prolonged operations on the cardiac, pulmonary and circulatory systems. During such operations, cannulas which are connected to the artificial heart-lung machine are first properly inserted through prepared incisions into the arterial and venous systems adjacent the heart, and even into the intracardiac chambers as well. Once properly positioned and in operation, the blood of the person is withdrawn or siphoned through the venous cannulas and pumped through the arterial cannulas back into the circulatory system by the artificial heart-lung machine. The heart and lungs of the person can thereby be effectively bypassed, thus allowing the surgeon to operate on the heart.

A major problem encountered in all such cardiac cannulation techniques involves the introduction of air into the circulatory system during the insertion and positioning of the various venous, arterial and intracardiac cannulas. In this regard, the avoidance of any such introduction is extremely important because of the danger of stroke or other adverse effects such air may have on the circulatory system.

The present state of the art provides two possible methods for avoiding any such introduction of air during cardiac cannulation. One method involves first inserting the distal end of the cannula into the circulatory system while the tubing connecting the cannula to the heart-lung machine is clamped shut by external means. The entrapped air is then vented by manipulating a drain line near the proximal end of the cannula thereby permitting the cannula to fill with the patient's blood. This method, however, does not prevent the possible introduction of air into the blood stream during initial insertion of the distal end of the cannula. In addition, it requires the extra steps of manipulating both the venting line and the external clamp, and cannot prevent the probable entrapment of air in the tube between this venting line and the clamp itself.

A second method of cannula insertion practiced in the present art involves first holding the cannula upright and filling it either with a serum or with blood through the plurality of holes near its closed distal tip. Then, the surgeon rapidly inserts the distal end of the cannula into the prepared incision in the circulatory system in order to avoid excessive spillage of the fluid, if at all possible. This method has its shortcomings both because of the mess created by the spilling fluid and because as the fluid empties, air may be again allowed into the cannula and later introduced into the circulatory system.

SUMMARY OF THE INVENTION

One embodiment of the present invention comprises a balloon-tipped extracorporeal cannula apparatus suitable for use in a cardiac cannulation technique including a first elongated and flexible tubular member having a proximal and a distal end, the proximal end being open, the distal being closed at its tip and including a plurality of holes near the distal end, an inflatable balloon on the inside wall of the first member adjacent to and proximal of the holes therein, and means including a second flexible tubular member contacting the balloon for readily inflating and deflating the balloon. When inflated, the balloon completely occludes the lumen of the first member and includes means for preventing the entrapment of any air near the distal end of the first member and for allowing fluid to wash freely across and through the unobstructed portion of the distal end of the first member after its insertion into the circulatory system.

A second embodiment of the present invention comprises a method for inserting a cannula during a cardiac cannulation technique comprising filling the lumen of a cannula with fluid, occluding the filled lumen of the cannula near the holes at the closed distal tip of the cannula, inserting the distal end of the filled and occluded cannula into the circulatory system of a person through a prepared incision and unoccluding the lumen thereby allowing fluid to flow between the cannula and the circulatory system.

The present invention permits cannulation of the heart and adjacent vessels without the risk of trapping any air near the distal end of the cannulas and thereby eliminates any possibility of introducing such air into the circulatory system during the cannulation. This is accomplished by positioning the intraluminal balloon so that the most distal portion of the balloon, when inflated, extends to a point between the most distal portion and the most proximal portion of the holes near the distal end of the cannula. This positioning eliminates both the need for manipulating any external venting line or tubing clamp and the mess and spillage of fluid characteristic of prior art methods. It further specifically prevents the entrapment of any air either distal of the holes in the closed distal tip of the cannula or proximal of the holes between the inflated balloon and the plurality of holes themselves, as would result with the use of catheters such as the ones disclosed in the Rocchi and Kim references.

The above positioning of the intraluminal balloon in the present invention also provides other advantages by only partially obstructing the holes near the distal end of the cannula. For instance, the distal tip of the cannula may become wedged or stuck in a side vein or artery or in an inner chamber of the heart during cannulation and thus threaten to occlude or block the vessel or chamber when such occlusion is both unexpected and not desirable. With the present invention, this result may be avoided because blood may still be able to wash or flow freely across and through the unobstructed portion of the distal end of the cannula after its insertion and before the balloon is deflated and the siphoning or pumping action begun. This provides a major advantage over such balloon catheters as disclosed in Rocchi, which completely obstruct the fluid holes in the catheter when the balloon is inflated thereby negating any possible bypass for the flow of blood if the cannula becomes unavoidably stuck.

In addition, if the inflated balloon completely obstructs the holes, it must also at least partially project through the holes thereby providing an increased possibility both that the balloon may rupture and that the balloon, when deflated, may hinder the free flow of fluid through both the holes and the lumen of the cannula.

One object of the present invention is therefore to provide a balloon-tipped extracorporeal cannula and method for its insertion that prevents the introduction of any trapped air into the circulatory system of the patient during cannulation.

Another object of the present invention is to provide a balloon-tipped extracorporeal cannula that allows fluid to wash or flow freely across and through the unobstructed portion of its distal end after insertion into the circulatory system and before the balloon is deflated.

Another object of the present invention is to provide a method for inserting a cannula during a cardiac cannulation which avoids the mess of fluid spillage and the need for external clamps or for venting trapped air in the cannula.

Related objects and advantages of the present invention will be apparent from the following description.

BRIEF DESCRIPTION OF THE DRAWINGS

FIG. 1 is a fragmented side elevation of the balloon-tipped extracorporeal cannula comprising a preferred embodiment of the present invention with a portion broken away to reveal the partially collapsed balloon.

FIG. 2 is a partial side elevation of the cannula in FIG. 1 with a portion broken away to reveal the balloon when inflated.

FIG. 3 is a cross-sectional view of the cannula in FIG. 1 taken along line 3—3.

FIG. 4 is a cross-sectional view of the cannula in FIG. 2 taken along line 4—4.

DESCRIPTION OF THE PREFERRED EMBODIMENTS

Figure 5:
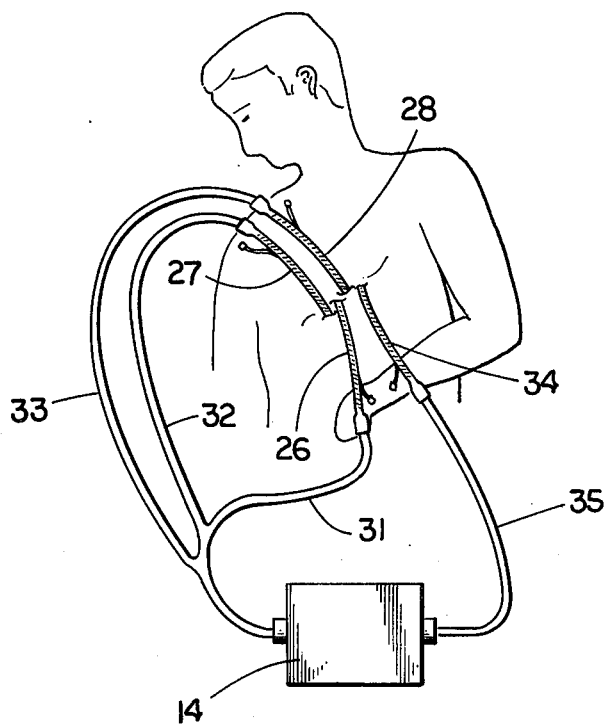
FIG. 5 is a reduced representation of four balloon-tipped extracorporeal cannulas of the present invention, as shown in FIG. 1, in use during a cardiac cannulation.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, the balloon-tipped cannula 10 comprising a preferred embodiment of the present invention is therein depicted. Cannula 10 includes a first elongated and flexible tube 11 which has both a proximal end 12 and a distal end 13. The proximal end of cannula 10 is open to allow the cannula to be attached to various secondary tubing which then connects the cannula to the desired equipment, such as the heart-lung machine 14 in FIG. 5. Distal end 13, on the other hand, has a closed and thickened distal tip 15 and includes a plurality of holes 16 near this distal tip which allow fluid to flow between the lumen 17 of cannula 10 and the circulatory system of the person.

As stated above, tube 11 of the preferred embodiment is made of a flexible material, such as rubber or polyvinyl. It also includes a spiraling wire 18 which is molded into the cannula wall 24. This wire 18 reinforces the central portion of cannula 10 thereby facilitating easy handling and preventing any possibility of the cannula collapsing or being pinched shut and thus closing off the flow of blood to or from the patient. Other ways of reinforcing the tubular body of a cannula are known in the art and will adapt equally well to the present invention. In addition, no reinforcement may be needed if the tube material is sufficiently strong.

The dimensions of tube 11 may vary greatly according to the person's age and size, the number of cannulas used in the cannulation technique and the specific manufacturer of the cannulas used. The external cross-sectional diameter of the tube 11 may thus vary from about 1 cm. to about 2 cm. at its widest point, tube 11 of the preferred embodiment being about 1.5 cm. in diameter.

An inflatable balloon 21 is positioned on the inside wall of tube 11 adjacent to and proximal of the holes 16. A second elongated and flexible tube 22 is connected to inflatable balloon 21 through an orifice or opening 23 in the cannula wall 24. Tube 22 then connects the balloon 21 to a supply of fluid (not shown) which is used to inflate and deflate the balloon during use of the cannula 10. Air may be used as a satisfactory inflating substance, however, it is desirable to use a liquid such as a saline solution because of the possible danger of a leak developing in the balloon which then could introduce the air into the circulatory system of the person.

Although various fluid supplies and means of inflating and deflating balloon 21 may be used in conjunction with the present invention, in the preferred embodiment tube 22 connects to a female attachment or adapter 19 which receives a standard syringe (not shown). This syringe is used to inject or withdraw fluid through tube 22 thereby inflating and deflating the balloon.

In constructing a balloon-tipped extracorporeal cannula pursuant to the present invention, inflating tube 22 may extend completely along the inside or outside of cannula tube 11. However, cannula 10 of the preferred embodiment incorporates the inflating tube or lumen 22 into the cannula wall 24 through the major portion of tube 11, as better shown in FIG. 3. Tube 22 of the preferred embodiment is thereby also protected by reinforcing wire 18 before it finally exits the cannula wall near the proximal end 12 of tube 11.

When deflated, collapsible balloon 21 lies flush against the inside wall of tube 11 thereby allowing fluid to flow freely through cannula 10 with a minimal amount of turbulence. The caliber or size of the deflated balloon 21 as it lies against the wall is such that it provides no appreciable blockage of the lumen cavity 17 or the fluid passing therethrough. In FIGS. 1 and 3, balloon 21 is shown not completely deflated for the convenience and understanding of the reader and thus obstructs the lumen 17 substantially more than when fully deflated.

Figure 6:
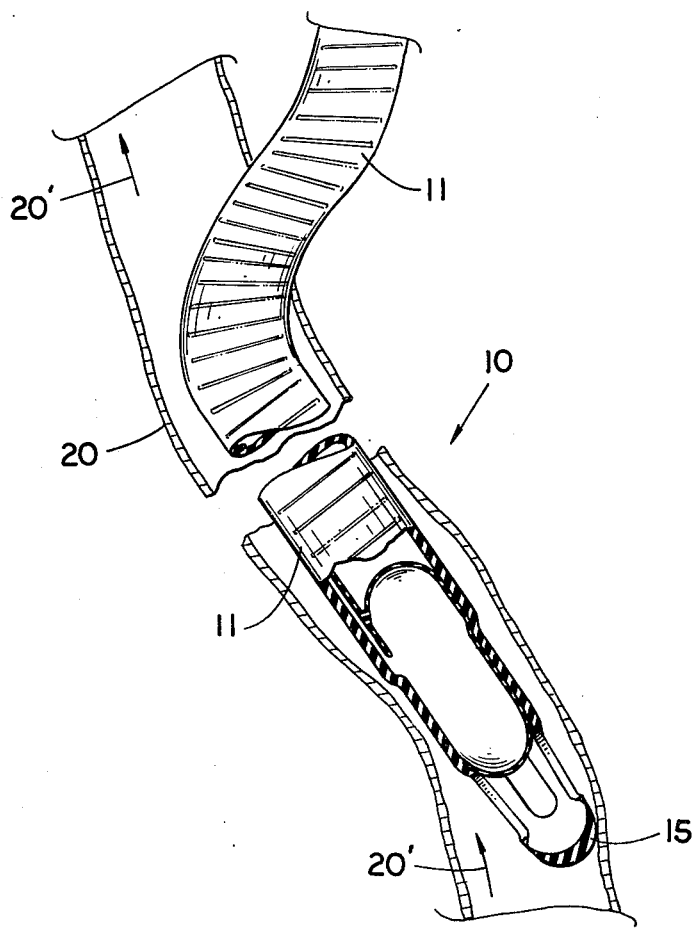
FIG. 6 is a part-sectional view of the distal end of the cannula in FIG. 2 positioned in the inferior vena cava adjacent a person's heart during a cardiac cannulation.

When inflated, as shown in FIGS. 2, 4, and 6, balloon 21 completely occludes the lumen 17 of cannula 10. The most distal portion 25 of the balloon 21 also extends to a point between the most distal portion and most proximal portion of the holes 16 near the distal end of tube 11. FIG. 4 depicts a cross-sectional view of cannula 10 in FIG. 2 taken at the most proximal portion of the holes 16. As it reveals, the inflated balloon completely occludes the cannula lumen at that point thereby preventing the flow of any fluid through the cannula. More importantly, by occluding the lumen 17 right up to the holes 16, the inflated balloon also prevents the entrapment of any air in the tube 11 proximal of holes 16 and thereby avoids the possible introduction of any such entrapped air into the circulatory system upon insertion of the cannula.

As previously discussed, an additional feature of the balloon-tipped extracorporeal cannula of the present invention is that the inflated balloon only partially obstructs the holes 16 near the distal end 13 of the cannula. Therefore, no air can be trapped in the closed distal tip during insertion, and the person's blood may be able to wash or flow across and through the unobstructed portion of the distal end of tube 11 if it becomes wedged or stuck in a vessel or chamber after its insertion and prior to deflation of the balloon 21. This minimizes the possibility of interference with normal blood flow prior to initiating the artificial heart-lung action and thus provides less chance of clots or other tissue building up on the cannula tip and thereby impairing or blocking the flow of blood through the circulatory system. FIG. 6 depicts a venous cannula 10 of the present invention positioned in an inferior vena cava 20 during a cardiac cannulation and prior to deflation of the balloon. The blood is flowing in the direction of arrow 20'.

A second preferred embodiment of the present invention comprises a method of inserting balloon-tipped extracorporeal cannula 10 into a person's circulatory system during a cardiac cannulation technique. The first step in this method involves filling the lumen 17 of the cannula 10 with a fluid. For this purpose, the fluid may be either blood or a compatible serum such as a saline solution and the filling may be accomplished through either the proximal or distal end of the cannula. In the preferred embodiment, the cannula 10 is filled with a saline solution through the holes 16 near the closed distal tip.

The next step is occluding the lumen 17 near the holes 16 at its closed distal tip 15 by inflating balloon 21. The distal end of the filled and occluded cannula 10 is then inserted into the circulatory system of the person through a prepared incision. And lastly, the lumen 17 is unoccluded by deflating balloon 21 thereby allowing fluid to flow between the cannula and the circulatory system of the person.

FIG. 5 depicts the preferred method and balloon-tipped extracorporeal cannula 10 of the present invention in use during a cardiac cannulation. Venous cannulas 26 and 27, constructed according to the present invention, are first positioned in the superior and inferior vena cavae, respectively. An intracardial cannula 28 is also positioned inside the left ventricle of the heart in order to decompress the heart and keep the level of blood in it low thereby preventing any possibility of the heart distending during the operation. These cannulas are in turn connected through tubing 31, 32 and 33, respectively, to the input side of a heart-lung machine 14. An arterial cannula return line 34 is then positioned in the aorta or femoral artery in order to recirculate the blood from the heart-lung machine 14 through tubing 35 and back into the circulatory system of the person.

In practice, both the number and location of the cannulas used in a cardiac cannulation technique can vary according to a variety of factors, such as the specific type of operation involved. In the preferred embodiment, four cannulas are used in order to assure proper and complete cannulation. The cannulas are first properly inserted into the circulatory system according to the above-described method. Then, when all four are properly positioned, the balloons are deflated and the siphoning and recirculating action through the heart-lung machine 14 is begun. At this time, the surgeon can operate on the person's heart, lungs or adjacent vessels while the machine 14 artificially maintains the heart and lung functions. When the operation is completed, the cannulas are again occluded by inflating the intraluminal balloons thus allowing the person's heart and lungs to resume their normal functions.

As shown by the above disclosure, the method and balloon-tipped cannula of the present invention permit cannulation of the heart and vessels without the risk of introducing trapped air into the circulatory system, as commonly experienced in the prior art. The present invention also eliminates the need for external cannula manipulation, such as the venting of trapped air, or the use of clamps to block the secondary tubing while the cannula fills with fluid.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A balloon-tipped extracorporeal cannula apparatus suitable for use in a cardiac cannulation technique comprising:
   (a) a first elongated and flexible tubular member having a proximal and a distal end, the proximal end being open, the distal end being closed at its tip and including a plurality of holes near the distal end;
   (b) an inflatable balloon on the inside wall of said first member adjacent to and proximal of the holes therein, said balloon, when inflated, completely occluding the lumen of said first member and including means for preventing the entrapment of any air near the distal end of said first member and for allowing liquid to wash freely across and through the unobstructed portion of the distal end of said first member upon insertion of the distal end into the circulatory system of a person;

(c) and means including a flexible tubular passageway communicating with said balloon for readily inflating and deflating said balloon.

2. A balloon-tipped extracorporeal cannula apparatus suitable for use in a cardiac cannulation technique comprising:

(a) a first elongated and flexible tubular member having a proximal and a distal end, the proximal end being open, the distal end being closed at its tip and including a plurality of holes near the distal end;

(b) an inflatable balloon on the inside wall of said first member adjacent to and proximal of the holes therein, said balloon, when inflated, completely occluding the lumen of said first member and including means for preventing the entrapment of any air near the distal end of said first member and for allowing liquid to wash freely across and through the unobstructed portion of the distal end of said first member upon insertion of the distal end into the circulatory system of a person, said means for preventing and for allowing being that the most distal portion of the balloon, when inflated, extends to a point between the most distal portion and the most proximal portion of the holes near the distal end of said first member; and (c) means including a second flexible tubular member contacting said balloon for readily inflating and deflating said balloon.

3. The apparatus of claim 1 wherein said first member is about at least 1.5 centimeters in external diameter.

4. The apparatus of claim 1 wherein said means for readily inflating and deflating additionally comprises means for connecting the end of said second member opposite said balloon with a medical syringe.

5. The combination comprising:
(a) a heart-lung machine means;
(b) and the cannula apparatus of claim 1 connected to said machine means.

6. The combination of claim 5 wherein the means for preventing and for allowing is that the most distal portion of the balloon, when inflated, extends to a point between the most distal portion and the most proximal portion of the holes near the distal end of said first member.

7. The apparatus of claim 6 wherein said means for readily inflating and deflating additionally comprises a medical syringe filled with fluid and means for connecting said syringe with the end of said second member opposite said balloon.

8. A method for inserting a cannula during a cardiac cannulation technique comprising:

(a) filling the lumen of a cannula with liquid, the cannula including a first elongated and flexible tubular member defining the lumen therein and having a proximal and a distal end, the proximal end being open and the distal end including a plurality of holes near the end thereof;

(b) occluding the filled lumen of the cannula near the holes at the distal end of the cannula, said occluding comprising inflating a balloon on the inside wall of the first member adjacent to and proximal of the holes therein, said occluding further being as to prevent the entrapment of any air near the distal end of the first member while allowing liquid to wash freely across and through the unobstructed portion of the distal end upon insertion thereof into the circulatory system of a person;

(c) inserting the distal end of the filled and occluded cannula into the circulatory system of a person through a prepared incision;

(d) and unoccluding the lumen of the cannula thereby allowing liquid to flow between the cannula and the circulatory system, said unoccluding comprising deflating the balloon on the inside wall of the cannula.

9. The method of claim 8 wherein said inflating is to an extent that the most distal portion of the balloon extends to a point between the most distal portion and the most proximal portion of the holes thereby preventing the entrapment of any air near the distal end of the cannula during said inserting.

10. The method of claim 9 wherein the distal end of the cannula is closed at its tip, said filling being accomplished through the holes near the closed distal tip of the cannula.

11. A balloon-tipped extracorporeal cannula apparatus suitable for use in a cardiac cannulation technique comprising:

(a) a first elongated and flexible tubular member having a proximal and a distal end, the proximal end being open and the distal end including a plurality of holes near the end thereof;

(b) an inflatable balloon on the inside wall of said first member adjacent to and proximal of the holes therein, said balloon, when inflated, completely occluding the lumen of said first member and including means for preventing the entrapment of any air near the distal end of said first member and for allowing liquid to wash freely across and through the unobstructed portion of the distal end of said first member upon insertion of the distal end into the circulatory system of a person; and (c) means including a flexible tubular passageway communicating with said balloon for readily inflating and deflating said balloon.

12. The apparatus of claim 11 wherein said means for preventing and for allowing is that the most distal portion of the balloon, when inflated, extends to a point between the most distal portion and the most proximal portion of the holes near the distal end of said first member.

* * * * *